US008812588B2

(12) United States Patent
Dutton et al.

(10) Patent No.: US 8,812,588 B2
(45) Date of Patent: Aug. 19, 2014

(54) COMPUTER PROGRAM, METHOD, AND SYSTEM FOR COLLECTING AND ANALYZING DATA FOR SPECIAL NEEDS CHILDREN

(75) Inventors: Riley Grant Dutton, Wichita, KS (US); Gary W. Singleton, Wichita, KS (US)

(73) Assignee: Heartspring, Inc., Wichita, KS (US)

( * ) Notice: Subject to any disclaimer, the term of this patent is extended or adjusted under 35 U.S.C. 154(b) by 305 days.

(21) Appl. No.: 13/475,699

(22) Filed: May 18, 2012

(65) Prior Publication Data

US 2013/0311538 A1 Nov. 21, 2013

(51) Int. Cl.
*G06F 15/16* (2006.01)

(52) U.S. Cl.
USPC .......................................... 709/203; 709/219

(58) Field of Classification Search
USPC .......... 709/203, 206, 217–219; 434/236–238; 705/2–3
See application file for complete search history.

(56) References Cited

U.S. PATENT DOCUMENTS

| 6,266,788 | B1 * | 7/2001 | Othmer et al. ............. 714/38.11 |
| 6,633,223 | B1 * | 10/2003 | Schenker et al. ............ 340/5.53 |
| 6,905,883 | B1 | 6/2005 | Olmstead |
| 7,882,041 | B2 * | 2/2011 | Gibbons et al. .............. 705/326 |
| 8,140,627 | B2 * | 3/2012 | Lasensky et al. ............. 709/206 |
| 8,161,419 | B2 * | 4/2012 | Palahnuk et al. ............. 715/781 |
| 2007/0055545 | A1 * | 3/2007 | Maughan et al. ................ 705/2 |
| 2007/0165649 | A1 * | 7/2007 | Moritz .................... 370/395.64 |
| 2007/0180428 | A1 | 8/2007 | Behrmann et al. |
| 2008/0114771 | A1 * | 5/2008 | Welingkar et al. ............. 707/10 |
| 2008/0155090 | A1 * | 6/2008 | Ruscin et al. ................ 709/224 |
| 2008/0187893 | A1 * | 8/2008 | Blaustein et al. ............. 434/236 |
| 2008/0228882 | A1 * | 9/2008 | Lasensky et al. ............. 709/206 |
| 2012/0009894 | A1 * | 1/2012 | Franco et al. ............... 455/404.2 |
| 2012/0030257 | A1 * | 2/2012 | Conder et al. ................ 707/812 |
| 2013/0060744 | A1 * | 3/2013 | Roychoudhuri et al. ..... 707/706 |
| 2013/0311538 | A1 * | 11/2013 | Dutton et al. ................ 709/201 |
| 2013/0344470 | A1 * | 12/2013 | Morgan et al. ............... 434/350 |

* cited by examiner

*Primary Examiner* — Brendan Higa
(74) *Attorney, Agent, or Firm* — Hovey Williams LLP

(57) ABSTRACT

A computer program for directing operation of a computer system for use in collecting data for special needs students. The computer program comprises a code segment for receiving data representative of an incident for a special needs student from a portable electronic device operated by a first person; and a code segment for sending a notification of the incident to a portable electronic device operated by a second person to prevent duplicate reporting of the incident by the first and second persons.

16 Claims, 19 Drawing Sheets

*Diagram*
*1a: A sample student's profile page on the system*

A Test

About Me

| | | |
|---|---|---|
| Basic Info | Case Number | 852369 |
| | Birthday | November 9, 1995 (Age: 16) |
| | Enrollment Date | October 25, 2009 |
| | Food Record? | No |
| Important Dates | 3 Year Eval. | October 15, 2014 |
| | IEP Date | January 15, 2011 |
| Demographic Info | Edu. Diagnosis | AM - Autism |
| | Federal Ethnicity | White |

Guardians

| | | |
|---|---|---|
| Father | Name | John Test |
| | Address | 159 West Street |
| | | Toledo, OH 12345 |
| | Phone 1 | 316-634-8752 |
| | Phone 2 | 316-634-8754 |
| | Cell Phone | 316-890-4589 |
| | Fax | 316-634-8791 |
| | Email | john.test@yahoo.com |
| Mother | Name | Mabel Test |
| | Address | 159 West Street |
| | | Toldeo, OH 12345 |
| | Phone 1 | 316-634-8752 |
| | Cell Phone | 316-519-8756 |
| | Email | mabel.test@yahoo.com |

Agency Contacts

| | | |
|---|---|---|
| Northwest Special Education Coop | Name | Jane Doe (SPED Director) |
| | Address | 1234 ABC Street |
| | | Toledo, OH 12345 |
| | Phone 1 | 316-634-8756 |
| | Fax | 316-634-8851 |
| | Email | jdoe@nwsped.org |
| DDD | Name | Sam Jones |
| | Address | 4321 DEF Street |
| | | Toledo, OH 12345 |
| | Phone 1 | 316-634-8888 |
| | Fax | 316-634-4587 |
| | Email | sjones@DDD.org |

Sidebar:
- Edit Student Profile
- Student Schedule
- Student Files
- Student Menu
- Food Record
- Communication Log

Fig 3

*Diagram*
*2a: Behavior data collection setup*

Fig 4

*Diagram 2b: Editing a specific behavior tracker*

Data Collection　　　　　　　　　　　　　　　　　　　　　　　　　　　　　　　　Back to Tracker Setup

Daily Tracker for A Test Student

|  |  |
|---:|---|
| Label: | AGG |
| Type: | Frequency |
| Description:<br>Shown to staff for further clarification | This is a sample aggression frequency tracker. |
| Start Tracking On: | 2011-08-16 |
| Stop Tracking On: |  |
| Probes: |  |
|  | + Add New Probe |
|  | Save |

Fig 5

*Diagram 3a: Editing an individual therapy goal*

Therapy Data

View All Goals

| | |
|---:|:---|
| Label: | OT: Washing body |
| Short Description:<br>*Two to three sentences* | Record each body part that Izzy washes independently. |
| Long Description:<br>*A longer set of instructions* | 1. Have Izzy's visual support where she can see it.<br>2. Wait 10 seconds for Izzy to complete washing her body.<br>3. If she does not independently initiate then |
| Start Showing On: | 2011-11-01 |
| Stop Showing On: | 2012-03-01 |
| Prompt Level for Plus:<br>*This level or higher is a plus* | Independent |
| Trials per Session<br>*0 means infinite* | 1 |
| % for Plus<br>*Percentage of +/- and prompt components that have to be a "plus" for the whole trial to be a "plus"*<br>*Enter number only, no % sign* | 100 |
| Testing Mode<br>*Not shown to paraeducators, etc.* | ☐ |
| Highlight? | ☐ |
| | Save |

Fig. 7

*Diagram 4b: An example medication log for a Test Medication*

Medication Log for Test Medication @ 10:30 20mg (A Test Student)

| Date/Time Given | Given By | Confirmed By | Held? | Notes |
|---|---|---|---|---|
| 02/06/2012 08:32 | Riley Dutton | | Yes | Test (Left With Staff) |
| 01/11/2012 07:49 | Court Smith | | Yes | |
| 01/11/2012 07:49 | Court Smith | 5 | No | |
| 01/09/2012 13:52 | Riley Dutton | | Yes | |
| 01/09/2012 13:50 | Riley Dutton | | No | |
| 01/09/2012 13:50 | Riley Dutton | | Yes | |
| 01/09/2012 13:50 | Riley Dutton | | No | |
| 01/09/2012 11:59 | Riley Dutton | | No | |
| 01/09/2012 11:58 | Riley Dutton | | Yes | |
| 01/09/2012 11:58 | Riley Dutton | | No | |
| 01/09/2012 11:53 | Riley Dutton | | No | |
| ~~01/09/2012 11:27~~ | Riley Dutton | | No | |
| 01/06/2012 13:55 | Riley Dutton | RD | No | Medication |

Fig 9

*Diagram 4a: Editing a medication entry for a student*

Medication

Medication for A Test Student

Label: Test Barcode Required

Dosage: 20mg

Time Given: 15:00

Given On: Every Day

Notify:
Notify medical staff if not given within hours:minutes

Require Barcode: ✓
Require barcode to be scanned when giving medication.

Description: This is a medication that has a required barcode.
Shown to staff for further clarification

Start Administering On: 2011-11-02

Stop Administering On:

Save

Fig 10

Health Information

Fever 0
    Diarrhea 0
    Seizures 0
    Menstrual Cycle 0
    Vomiting 0
    Was nurse contacted? No
    Reason/Comments:
    Was PRN given? No
    What and when?

Note   Submitted By   Submitted On

Meal Information

Breakfast

Ate breakfast? No
    Fresh Fruit (1 each)
    Cereal of Choice (1 each)
    Pizza Brkfst Secondary (1 each)
    Milk - Variety (1 each)
    Breakfast comments

Lunch

Ate lunch? No
Hot Dog on a Bun (2 each)
Baked Beans H-39 (1/2 c)
Apples (fs) (1 each)
Ketchup (2 each)
Mustard (2 each)
Milk - Variety (1 each)
Lunch comments

Snack

Ate snack? No
Snack comments

Dinner

Ate dinner? No
Ham & Cheese Sandwichies (1 each)
Potato Salad (1/2 c)
Frosted Red Velvet Cake (1 each)
Milk - Variety (1 each)
Mustard (1 each)
Dinner comments

Activity Log

| Off-Campus Activities | Movies | Car Ride | Grocery Shopping | Mall | To the Park |
|---|---|---|---|---|---|
| Other Off-Campus | | | | | |
| On-Campus Activities | Gym | Movies | MSE Room | Party | Playground |
| Other On-Campus | | | | | |

Sleep

| Time | | | | | | | | |
|---|---|---|---|---|---|---|---|---|
| 9:30PM - 10:30PM Off Campus | Asleep | Awake, OOB | Awake, IB | Toileted | Bed Check | Behaviors | Soiled | Seizures |
| 10:30PM - 11:30PM Off Campus | Asleep | Awake, OOB | Awake, IB | Toileted | Bed Check | Behaviors | Soiled | Seizures |
| 11:30PM - 12:30AM Off Campus | Asleep | Awake, OOB | Awake, IB | Toileted | Bed Check | Behaviors | Soiled | Seizures |
| 12:30AM - 1:30AM Off Campus | Asleep | Awake, OOB | Awake, IB | Toileted | Bed Check | Behaviors | Soiled | Seizures |
| 1:30AM - 2:30AM Off Campus | Asleep | Awake, OOB | Awake, IB | Toileted | Bed Check | Behaviors | Soiled | Seizures |
| 2:30AM - 3:30AM Off Campus | Asleep | Awake, OOB | Awake, IB | Toileted | Bed Check | Behaviors | Soiled | Seizures |
| 3:30AM - 4:30AM Off Campus | Asleep | Awake, OOB | Awake, IB | Toileted | Bed Check | Behaviors | Soiled | Seizures |
| 4:30AM - 5:30AM Off Campus | Asleep | Awake, OOB | Awake, IB | Toileted | Bed Check | Behaviors | Soiled | Seizures |
| 5:30AM - 6:30AM Off Campus | Asleep | Awake, OOB | Awake, IB | Toileted | Bed Check | Behaviors | Soiled | Seizures |
| 6:30AM - 7:30AM Off Campus | Asleep | Awake, OOB | Awake, IB | Toileted | Bed Check | Behaviors | Soiled | Seizures |

Morning Shift Information

Complete body check performed at?
Student awoke at?
Was anything new added to the skincheck today? No
BM description:
BM count:
Items picked up in bedroom? No
No soiled/wet linens in hamper? No
Blinds open? No
Bed made? No
Does student have communication system? No
Did special incident occur? No

Fig 11B

Number of occurrences: 0
In general, how was the student's morning?
Items sent to school today:

Classroom Shift Information

Complete body check performed at?
Was anything new added to the skincheck today? No
BM description:
BM count:
Did student have communication system? No
Was schedule followed? No
Were goals complete? No
If not, why?
Did special incident occur? No
Number of occurrences: 0
In general, how was the student's school day?
Items sent home today:
Items needed tomorrow:

Evening Shift Information

Complete body check performed at?
Student went to sleep at?
Was anything new added to the skincheck today? No
BM description:
BM count:
Did student have communication system? No
Was schedule followed? No
Were goals complete? No
If not, why?
Did special incident occur? No
Number of occurrences: 0
In general, how was the student's afternoon/evening?

Fig 11C

*Diagram 6b: The steps in collecting Therapy Data using the client app. The goal to be run is chosen from a list; a number of trials are performed; then the session is completed by submitting notes for later review.*

COMPUTER PROGRAM, METHOD, AND SYSTEM FOR COLLECTING AND ANALYZING DATA FOR SPECIAL NEEDS CHILDREN

BACKGROUND

Many children have learning challenges, communication problems, emotional and behavioral disorders, physical disabilities, developmental disorders, and/or other special needs. Children with these kinds of special needs often benefit from additional and/or different educational services often referred to as "special education" services. Children with acute special needs often attend private schools or other institutions dedicated to serving and helping such children.

To assist with the diagnosis, treatment, and management of special needs children, schools and other institutions often collect and analyze data related to the behaviors, therapies, and administered medications for the children. Traditionally, such data has been collected manually with hash marks made on paper sheets. These paper sheets are then given to assistants to manually enter into programs (such as Microsoft Excel) that are not specifically designed to analyze the data.

SUMMARY

Applicant has discovered that the above-described manual collection processes are laborious and error-prone. Manual data collection methods can also lead to duplicate or missing data when different people concurrently collect data for the same children. In addition, the collected data lacks built-in integrity checks, and there is no way to know at exactly what time and by whom the data was collected.

Manual analysis of the collected data is also time consuming, with delays often measured in weeks between the time the data is collected and when it is able to be viewed for analysis after being compiled and entered into spreadsheets. Most software is not specifically designed to analyze this type of data, so teachers and medical professionals are limited in the way the data can be analyzed.

The present invention solves at least some of the above-described problems and provides a distinct advance in the art of data collection and analysis for special needs children by providing a computer program, method, and system designed specifically for this purpose.

An exemplary embodiment of the invention consists of two parts: a server which allows professional staff such as psychologists, therapists, teachers, etc. to setup specific data to be collected for a student and that analyzes the data once collected; and a plurality of mobile clients that allow multiple paraprofessionals such as medical assistants, education assistants, etc. to collect data simultaneously from anywhere in the world and transmit that data in real-time back to the sever for analysis.

In many schools and other institutions, multiple paraprofessionals and other users collect data on students at the same time across a wide area such as a campus. Embodiments of the invention are designed to facilitate collection of data by multiple persons simultaneously by:

Allowing an unlimited number of mobile clients to communicate with the server.
  Syncing data to the server and then updating the mobile clients whenever data has changed.
  Informing other users when data is collected on a student they are tracking, via real-time alerts.
  Informing users when the last time a medication was given or a therapy goal was run with a student by any staff member.
  Providing tools for professional staff to correct and/or delete data after it is collected. The system tracks what modifications are made to the data, when they are made, and who made them, to serve as an audit trail.

The present invention also provides mechanisms to ensure that the simultaneous collection of data by multiple users does not generate duplicate or redundant data:

As data is sent to the server in real-time, a notification of the collected data is sent to all connected mobile clients, resulting in the display of a "bubble" notification. For example, if John and Mary are collecting data on student Billy, when John sends data that indicates an aggression has occurred, a bubble appears on Mary's mobile device to indicate that John collected data on the aggression. This helps prevent duplication of data caused by two staff members submitting data at once.
  During analysis of incoming data by the server, an algorithm determines the likelihood of a piece of data being duplicated (based on factors such as multiple staff members recording the same behavior within a certain time frame). If a piece of data is determined to be duplicate, it is discarded.

When reviewing data for a student, professional staff are able to see that data in aggregate, but can also choose to look at the individual pieces of data collected, which tells them which staff member collected the data, at what time, and where. Staff members can make modifications to these specific data points to correct for inaccuracies in the data.

The present invention also provides improved mechanisms for analyzing data after it has been collected. The server processes data as it arrives in real-time, and then acts on the data through a series of algorithms. Some examples of this real-time analysis include:

Alerting professional staff when a behavior crosses a threshold of N occurrences in a specified time frame, or a behavior has lasted longer than N minutes.
  Alerting professional staff when a student has not been given medication at the correct time.
  Notifying professional staff if data seems "abnormal", based on factors including a rolling 10-day average for the data and the standard deviation for the data during the previous 10 days.

In some embodiments, the student data collected is accompanied by data representative of the staff member who collected the data, the time at which the data was collected, and the location where the data was collected. This data may be used to generate reports such as a heat map over a campus or other defined area showing where student behaviors are most prevalent. In addition, automatic alerts are triggered based on certain conditions, such as a student exiting out of a door during a time when they should be in a classroom, or a student getting too far away from a designated staff member.

The present invention is also unique in that it permits collection of data at any time and at any place. Rather than collecting behavior data as a "secondary" piece of information only when therapy is being performed with a student, the present invention provides for 24/7 collection of student data as a primary piece of information. Data collected during the same time frame (such as behavior data collected while a therapy session was in progress) can still later be linked together for joint analysis.

The present invention is also unique in that it enables the collection of data from a variety of disciplines, including psychology (behavior) data, therapy data, and medical data.

The data from these different disciplines is shared during reporting and analysis to give a more complete picture of a student's progress. For example, when looking at a graph of behaviors, psychologists can choose to see annotations on the graph indicating when medications were changed, or if a student's communication device was broken. The server can also automatically calculate correlations for behaviors compared to inputs from other disciplines such as amount of sleep, meals eaten, etc.

Embodiments of the invention also provide an important way to check the validity of data being collected. Professional staff using a mobile client are able to turn on a "Blind Data" mode. They can then collect data as normal. Later when the data is analyzed, the server automatically matches up data collected by paraprofessionals to the data collected by professional staff in "Blind Mode". The system calculates the percentage accuracy of the paraprofessional, allowing the professional staff to assess the validity of the data being collected. Such "Inter-rater" reliability data can be collected both for behavior data and therapy data.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 3 is an exemplary screen display that may be presented by one or more computer programs of the present invention.

FIG. 4 is another exemplary screen display that may be presented by one or more computer programs of the present invention.

FIG. 5 is another exemplary screen display that may be presented by one or more computer programs of the present invention.

FIG. 7 is another exemplary screen display that may be presented by one or more computer programs of the present invention.

FIG. 9 is another exemplary screen display that may be presented by one or more computer programs of the present invention.

FIG. 10 is another exemplary screen display that may be presented by one or more computer programs of the present invention.

FIG. 11B is another exemplary screen display that may be presented by one or more computer programs of the present invention.

FIG. 11C is another exemplary screen display that may be presented by one or more computer programs of the present invention.

Figure 1:
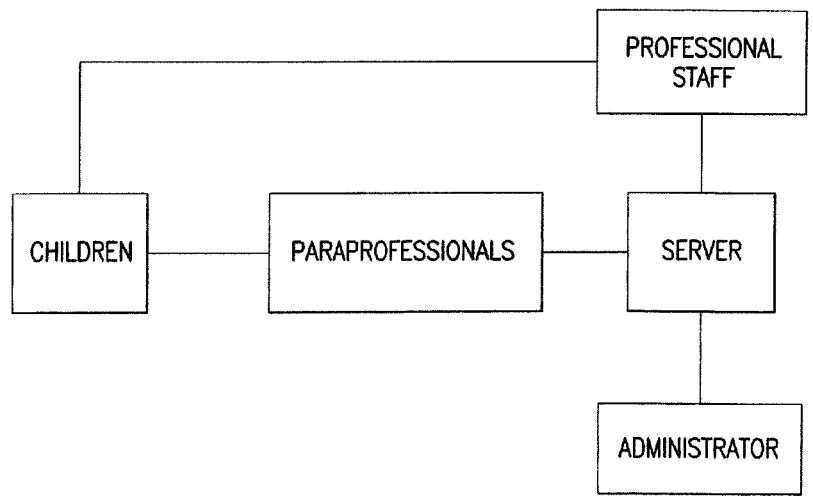
FIG. 1 is a block diagram that illustrates persons and/or entities that may be involved with aspects of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, act, etc. described in one embodiment may also be included in other embodiments, but is not necessarily included. Thus, the present technology can include a variety of combinations and/or integrations of the embodiments described herein.

FIG. 1 is a block diagram that illustrates the relationships between persons and/or entities that may be involved with aspects of the invention. The entities include at least one student, a number of paraprofessionals, at least one professional staff, and an administrator that operates a computer system. The invention may of course be used with any number of students, paraprofessionals, etc., but the description below focuses on one or two of each for purposes of describing embodiments of the invention.

The student or students may be children or any other persons in need of special education services. For example, a student may be a child with autism, Asperger's syndrome, cerebral palsey, or any other behavioral, developmental, and/or learning disability. "Students" and "children" are sometimes used interchangeably herein and refer to the same persons.

The paraprofessionals may be any persons who are trained to assist the professional staff but who do not themselves have professional degrees, licenses, etc. For example, the paraprofessionals may have training in physical therapy, education, and/or other skills. Typically, the paraprofessionals work with students under the direction of the professional staff.

The professional staff may be medical doctors, psychologists, psychiatrists, nurses, therapists, teachers and/or other persons who have professional training, education, and/or licenses in their areas of expertise.

Some aspects of the invention are preformed primarily by paraprofessionals, whereas other aspects are performed primarily by the professional staff. However, some aspects of the invention may be performed by either. As used herein, "persons", "users", "staff", and "staff members" may encompass paraprofessionals, professional staff, or both.

The administrator may be any person or entity that organizes and administers the activities of the students, paraprofessionals, and professional staff. The administrator may operate a computer system that can be accessed by the paraprofessionals, professional staff and/or others as described below. The administrator may be, for example, a school or institution such as Heartspring of Wichita, Kans.

In some embodiments, the persons and entities shown in FIG. 1 and described herein may be related or even combined. For example, the administrator may be an institution at which the paraprofessionals and professional staff work. Similarly, the paraprofessionals and professional staff may be the same persons.

Figure 2:
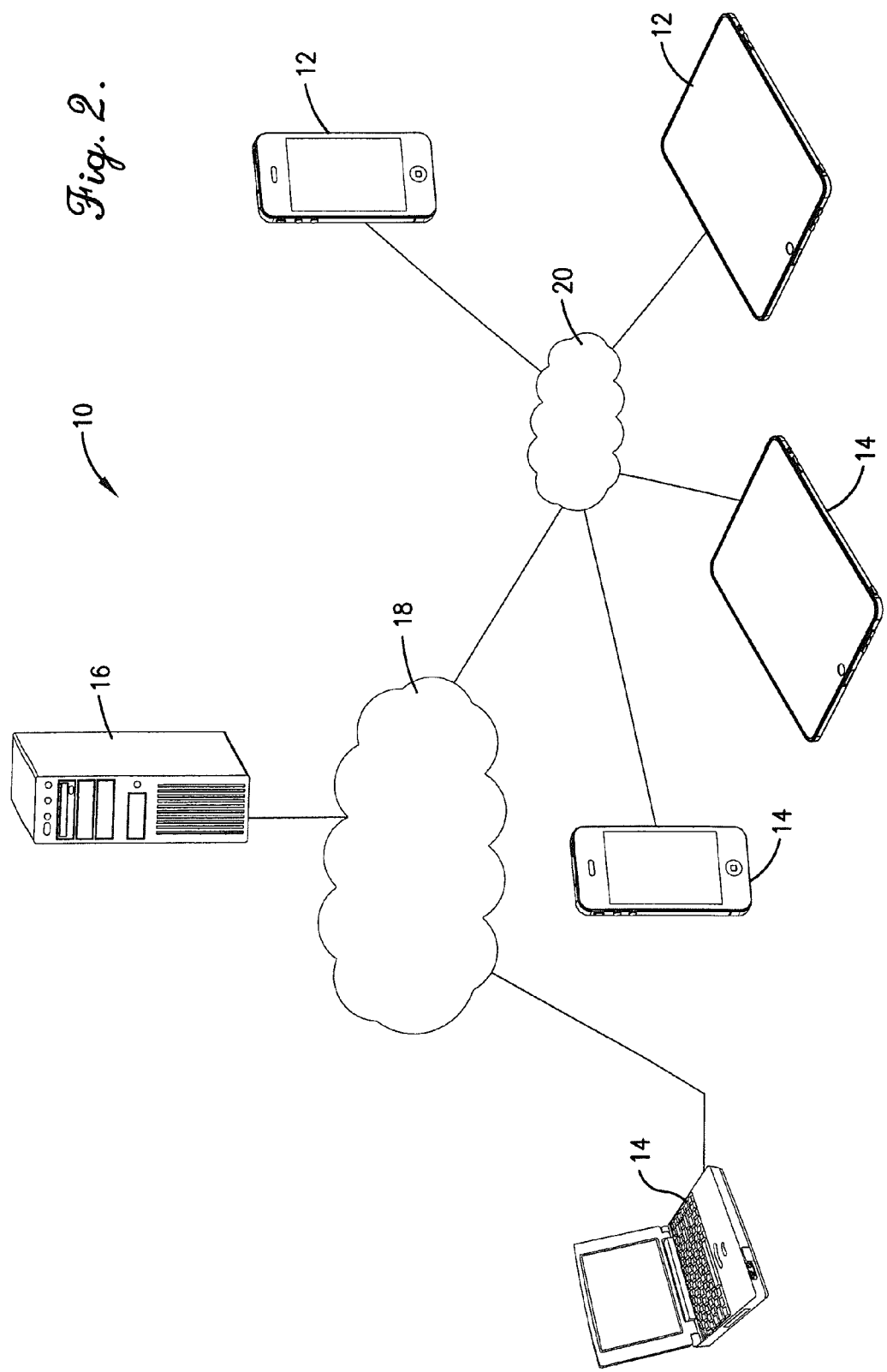
FIG. 2 is a schematic diagram of exemplary computer and communications equipment that may be used to implement embodiments of the invention.

Aspects of the invention can be implemented with computer hardware, software, firmware, or a combination thereof. In one embodiment, aspects of the invention may be at least partially implemented with a system of computer and communications equipment broadly referred to by the numeral 10 in FIG. 2. An embodiment of the computer and communications equipment 10 includes a number of portable electronic devices 12 operated by the paraprofessionals, a number of portable electronic devices 14 operated by or for the professional staff, a computer system 16 operated by or for the administrator, a communications network 18, and a wireless telecommunications network 20. The components of the computer and communication equipment 10 illustrated and described herein are merely examples of equipment that may be used to implement embodiments of the present invention and may be replaced with other equipment without departing from the scope of the present invention.

The portable electronic devices 12 may be any computer devices used by the paraprofessionals while working with the students. For example, the portable electronic devices 12 may be tablet computers or smart phones such as those sold by Apple®, Motorola®, Samsung® or Hewlett Packard®. The portable electronic devices may also be laptop computers or other portable computers. The portable electronic devices 12 include or can access an Internet browser and a conventional Internet connection such as a wireless broadband connection, a modem, DSL converter, or ISDN converter so they can access the computer system 16 via the communications networks 18 and/or 20. Embodiments of the portable electronic devices 12 may also include global navigation system receivers such as GPS receivers.

Likewise, the portable electronic devices 14 may be any computer devices used by the professional staff while working with the students and/or supervising the paraprofessionals. For example, the portable electronic devices 14 may be tablet computers or smart phones such as those sold by Apple®, Motorola®, Samsung® or Hewlett Packard®, laptop computers, or other portable computers. The portable electronic devices 14 include or can access an Internet browser and a conventional Internet connection such as a wireless broadband connection, a modem, DSL converter, or ISDN converter so they can access the computer system 16 via the communications networks 18 and/or 20. The portable electronic devices 14 may also include global navigation system receivers such as a GPS receivers.

The computer system 16 receives and stores data and other information from the portable electronic devices 12, 14 and other computer devices and transmits instructions, notifications, and other information back to the devices as described below. The computer system 16 also implements one or more computer programs for performing some of the functions described herein.

Embodiments of the computer system 16 may include one or more servers such as a web server, a database server, an application server, and/or an FTP server running Windows; LAMP (Linux, Apache HTTP server, MySQL, and PHP/Perl/Python); Java; AJAX; NT; Novel Netware; Unix; or any other software system. The computer system 16 includes or has access to computer memory and other hardware and software for receiving, storing, accessing, and transmitting data and other information as described below. The computer system 16 also includes conventional web hosting operating software, searching algorithms, an Internet connection, and is assigned a URL and corresponding domain name such as "heartspring.com" so that it can be accessed via the Internet in a conventional manner.

The number and type of servers in the computer system 16 is a matter of design choice and may depend on the number of students served by the computer system 16. Thus, the invention is not limited to the specific servers and other equipment described and illustrated herein. Similarly, any number of the portable electronic devices 12 and portable electronic devices 14 may be served by the computer system 16.

The computer system 16 may also host or store a database of all students, paraprofessional, and professional staff using the present invention. For example, the database may include the names, addresses, medical histories, age, sex, etc. of all the students and similar information for others. The computer system may also host and support software and services of proprietary mobile application providers such as Google, Apple, and Blackberry and may store the computer programs that are loaded on the portable electronic devices 12, 14.

The communications network 18 is preferably the Internet but may be any other communications network such as a local area network, a wide area network, or an intranet. The wireless network 20 may be any network capable of supporting wireless communications such as the wireless networks operated by AT&T, Verizon, or Sprint. The wireless network may include conventional switching and routing equipment. The communications network 18 and wireless network 20 may also be combined or implemented with several different networks.

Embodiments of the present invention also comprise one or more computer programs stored in or on computer-readable medium residing on or accessible by the portable electronic devices 12, 14 the computer system 16, or other computer equipment. The computer programs may comprise listings of executable instructions for implementing logical functions in the computer equipment. The computer programs can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can contain, store, or communicate the programs. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

An embodiment of the invention includes a program or programs that implement functions and features of the invention on the computer system 16. The computer system 16 and the computer programs implemented by it are referred to herein as the "server". Another embodiment of the invention includes one or more computer programs that implement functions and features of the invention on the portable electronic devices 12, 14. The portable electronic devices 12, 14 and the computer programs implemented by them are referred to herein as the "clients" or "mobile clients".

Server

The server allows paraprofessionals and professional staff to upload, view, and manage data and other information about students. In one embodiment, the server stores a student directory with comprehensive details on each student, including the student's demographic information, parental and district contact information, meal plan, related files (such as student support plan and IEP information), and information on data to be tracked for the student. An exemplary student profile is depicted in FIG. 3.

The server also features a comprehensive data analysis system to allow professional staff to review the results of collected data. The server also implements algorithms and processes for analyzing parts of the data automatically, in order to send alerts and provide important information in real-time to paraprofessional and professional staff.

Several types of data can be tracked by the server, including behavior data (or psychology data), therapy data (including speech, occupational, and physical therapy data), medical data, and general information about a student's day (the communication log).

Behavior Data

Behavior data is any data related to the field of psychology and includes information on behaviors exhibited by a student throughout the day, such as aggressions, self-injurious behaviors, or property destruction. After professional staff determine what behaviors are to be tracked as a part of a student's support plan, paraprofessionals and/or others may collect data on these behaviors throughout the day. The invention facilitates the real-time collection of this data along with pertinent information such as exactly what time the data was collected and by which paraprofessional or professional staff as described below.

Figure 4:
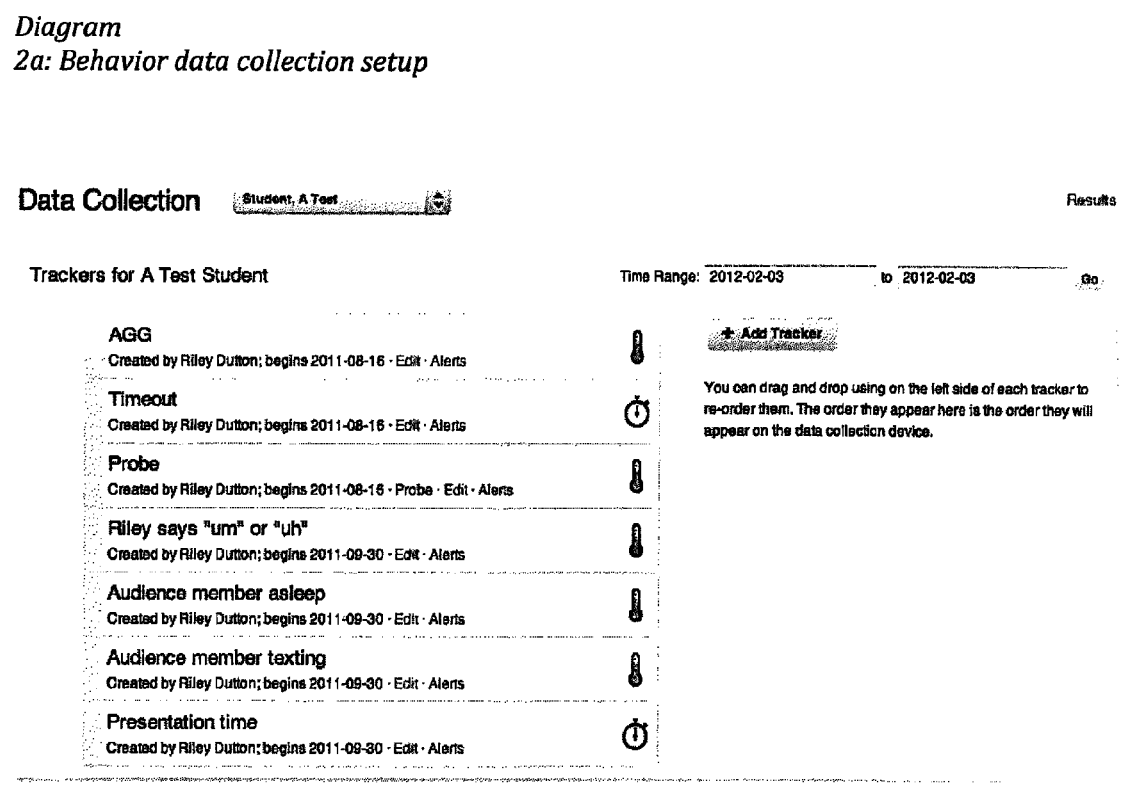

Professional staff also set up what "trackers" (behaviors) are to be monitored for each particular student. The professional staff can re-order the trackers to determine how they are displayed on the data collection client as shown in FIG. 4 and customize some of the following as depicted in FIG. 5:

The name of the tracker as it is displayed to paraprofessionals.

What type of data is to be tracked (a frequency count or a duration).

A description of the behavior which is shown to paraprofessionals, clarifying what should be tracked.

A start and end date during which the behavior should be tracked.

Probe times, which cause the behavior to be tracked during only certain parts of the day (for example, from 11:00 AM-12:00 PM and 3:00 PM-4:00 PM).

Once trackers are set up for a student, they are passed to at least one of the portable electronic devices 12 so that data can be collected.

Figure 6:
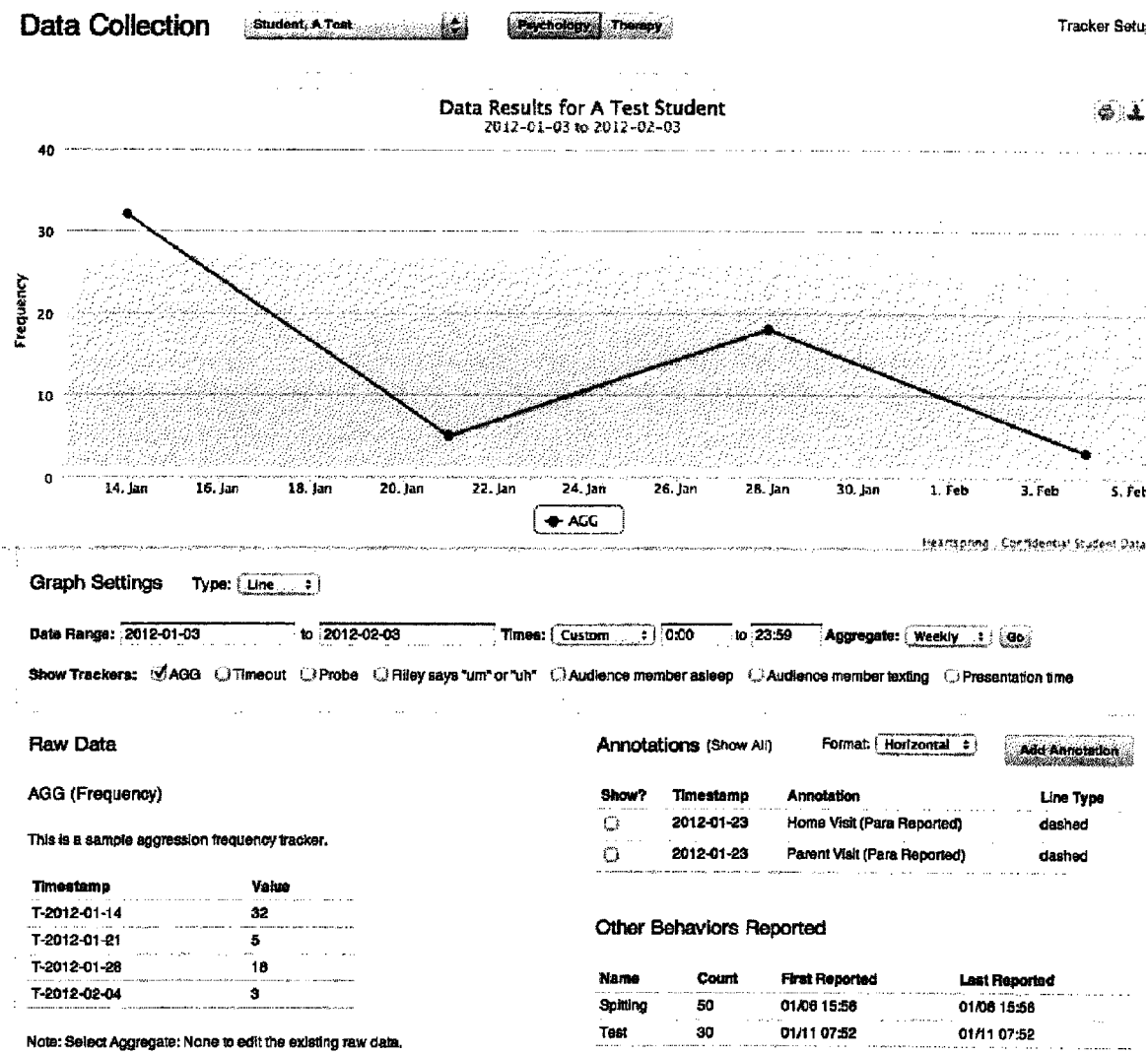
FIG. 6 is another exemplary screen display that may be presented by one or more computer programs of the present invention.

After sufficient data has been collected, the server automatically calculates the number and duration of behaviors that occurred for the selected trackers during the designated time frame. Professional staff and other users can analyze the data and calculations on the server using a graph-based front-end as shown in FIG. 6. This front-end allows users to:

Specify the date range, and inside that date range the specific times for which the data is to be analyzed.

Aggregate the data by Hour, Day, Week, Month, Year, or None (raw data).

Present the data in a graph and in table format. If "None" is selected for the Aggregate setting, a list of the specific data points collected including the exact time and person who collected the data is displayed.

Graph one or more behaviors on the same graph for comparison purposes.

Annotate the chart with vertical lines denoting specific events that are to be noted. These annotations are saved student-wide and are accessible by all staff for any chart (behavior or therapy). Some annotations are automatically generated by the server (such as when a paraprofessional or professional staff indicates that a student was off-campus with a parent). Others that are manually entered by staff include when medication changes were made, and when interventions or support plans were modified.

Present other relevant information such as other behaviors that were reported during data collection but are not being specifically tracked.

Analysis of inter-rater reliability data (also referred to as "blind data"). This is data that is collected by professional staff at the same time as it is being collected by paraprofessionals. The server stores this data separately, and then the front-end is capable of displaying a comparison between the two sets of data, showing the percentage difference. This is used for performing accuracy checks on the reliability of the data being collected by the paraprofessionals.

In addition to the analysis performed manually by professional staff, the server provides several mechanisms for automatic, real-time data analysis. For example, professional staff have the ability to set up alerts for trackers. These alerts can be triggered by either a number of occurrences within a specific time period (e.g., 5 reported aggressions within 2 minutes), or by a total duration of the behavior (e.g., a drop, which is when a student falls to the floor, that lasts longer than 5 minutes). If one of these alert thresholds has been crossed, the server automatically notifies professional staff via email and an alert on their portable electronic device if they are currently using one. The alerts are provided in essentially real-time as the data is being collected so appropriate action can be taken if warranted.

The server may also automatically calculate helpful information about the data being examined, including the standard deviation and a rolling 10-day average line to help determine trends. In addition, if "no data" is reported by a paraprofessional, this is indicated on the graph by a colored background to notify the professional staff that the data may be incomplete.

Therapy Data

Therapy data is data collected relating to the speech, physical, and occupational therapy fields. Goals may be periodically determined by professional staff for each student, along with objectives for achieving these goals. Professional staff develop a plan for achieving those goals by identifying specific skills to improve through repeated sessions of activities designed to improve those skills. The invention facilitates the collection of data during these sessions for faster analysis by the professional staff.

Professional staff are able to set up "goals" for each student as follows. A goal often correlates closely with an objective in a student's Individualized Education Plan (IEP). Each goal can be customized in the following ways as depicted in FIG. 7:

A name or label for the goal can be created for display on the portable electronic devices 12, 14.

A short description of the goal to serve as a brief reminder to staff.

A long description of the goal describing exactly how it is to be executed by the staff working with the student.

A date range during which the goal is active.

In the therapy field, there is a concept of "Prompt Level", which is the level of assistance required by the student to complete the task. Staff can customize at what prompt level the trial of the component is to be considered a success for data analysis purposes.

The number of trials to require for each session with the student.

The percentage of components that must be completed successfully in order to consider the overall trial a success.

In addition, each goal consists of a group of one or more components. Components are the specific skills targeted during the session with the student. There are 3 types of components:

Plus/Minus. This is the most basic type of component, which is used to indicate a simple "correct/incorrect" designation for the skill.

Prompt Level. This component is used when the professional staff want to know the amount of assistance required by the student to perform the skill.

Choices. This component is used to provide a customized list of choices to staff performing the trial with the student. It is not used for calculation of the success of a trial, but can be used to gather additional information for the therapist to manually analyze later.

When a staff runs a goal with a student, it is referred to as a "session". During the session, the staff performs a series of trials with the student. Each trial consists of performing each component with the student and recording the data for that component, depending on the instructions given and the type of component. For example, a component might be a Plus/Minus type and labeled "Says 'Hello' correctly." As the staff performs the trial with the student, they would mark "Plus" (or "correct") if the student says "Hello", or "Minus" (or "incorrect") if the student fails to perform the task correctly.

Figure 8:
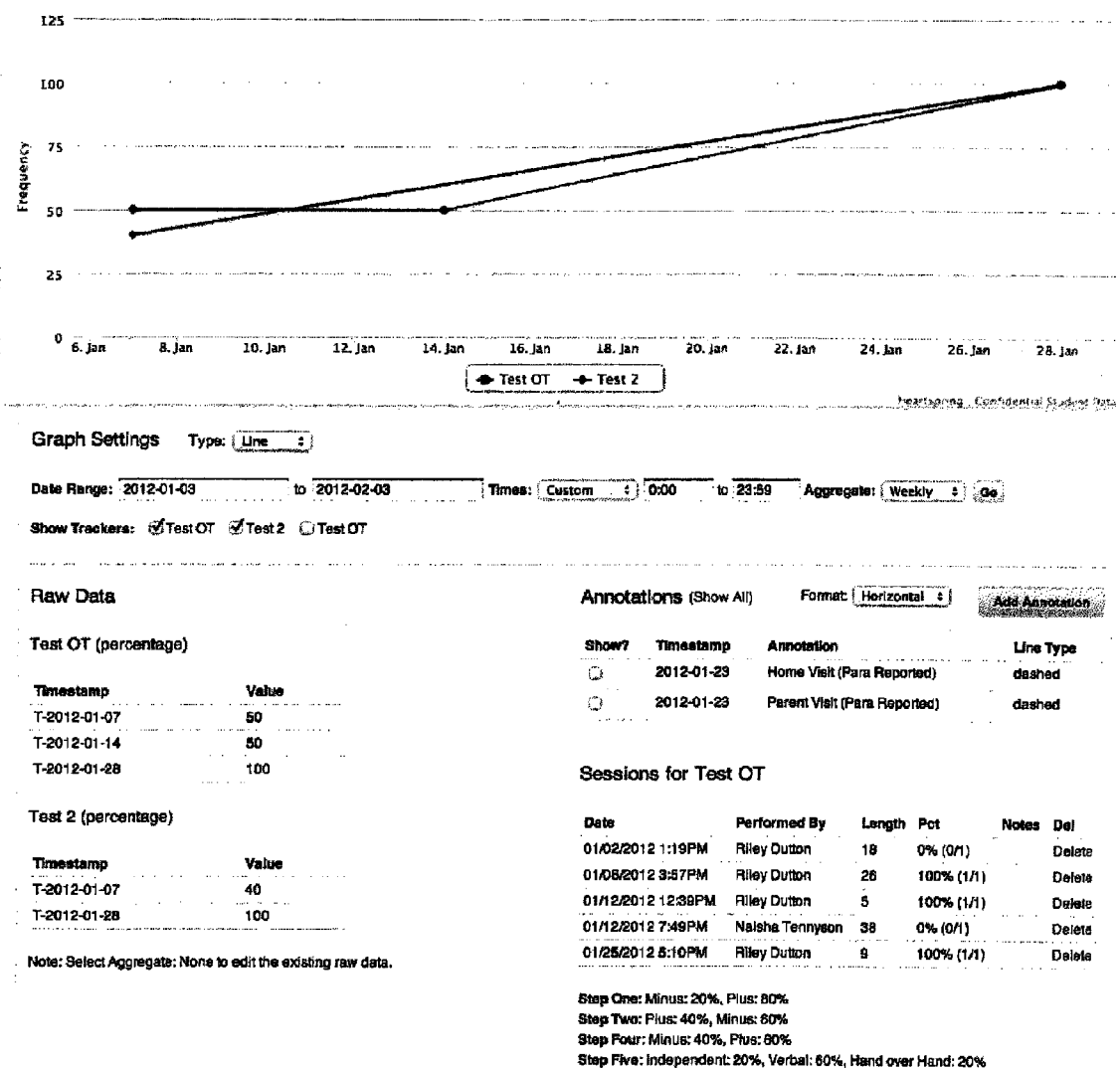
FIG. 8 is another exemplary screen display that may be presented by one or more computer programs of the present invention.

After sufficient data is collected, the server automatically calculates the percentage for each trial and session. This percentage is calculated by an algorithm based on the setup of the goal and its components. The result is then presented in a front-end depicted in FIG. 8, which is similar to the one described in the behavior data section above. In addition to the aspects of the behavior data analysis listed in the previous section, the front-end:

Allows users to view each session that was performed by a staff member, and see when it was started, how long it took to perform the session, and the overall percentage for that specific session, as well as the number of trials performed. Staff can also enter notes after the session has ended which are shown to the therapist, and may include additional pertinent information about the session.

Displays the automatically calculated percentages of total responses for each possible option of each component. This can be used by the professional staff to quickly check the integrity of the data.

Medical Data

The server also has the ability to track the medications that are given to each student throughout the day as depicted in FIG. 9. The server does not provide an electronic medical records system, but rather tracks the administration of medications to the students by paraprofessionals and professional staff and provides alerts to professional staff if a medication is given at the incorrect time or another medication error occurs.

Professional staff are able to set up medications for each student on the server as depicted in FIG. 10. The medications are able to be customized in the following ways:

Designate the student to which the medication is to be given.

Provide a label and dosage for the medication, used to identify it throughout the server.

Designate a time that the medication should be given. This is used to notify the professional staff administering the medication if it is being given at the incorrect time, and is also used to alert the professional staff if the medication is given at the incorrect time. The time field can also be left blank, which indicates that the medication can be given as-needed throughout the day.

Designate if the medication is to be given daily, only on weekdays or weekends, or every other day.

Specify a time interval after which the professional staff should be notified that the medication was not given. For example, setting "0:30" would cause an alert to be sent to the professional staff at 7:30 AM if a medication to be given at 7:00 AM had not yet been administered.

Toggle whether or not to require a barcode to be scanned before the medication can be given. The barcode scanning serves as a physical check to make sure that the correct medication is being given to the correct student at the correct time. More information on this is discussed in the Client section below.

A description of the medication, including any relevant dosage or administration instructions for staff to read before giving the medication.

A start and stop date during which the medication is to be administered to the student. This information is then sent to the portable electronic devices 12 and is used to let the paraprofessionals or professional staff track which medications have been administered and when.

The server provides a report that allows the professional staff to view the log of when each medication was given, at what time, and by which staff member. In addition, the server performs automatic analysis of the medication data as it arrives to send alerts to professional staff if a medication has been given at the incorrect time. A daily report may also be generated by the server that shows the professional staff an overview of all the medications being tracked, if they were given at the correct time or not, and if any notes were entered on the portable electronic device 12 when the medication was given.

Communication Log

The communication log is a set of general information about a student's day. It is filled out by paraprofessionals throughout the day, and reviewed by various professional staff including psychologists, medical staff, teachers, and therapists. An exemplary communications log is shown in FIG. 11A, 11B, 11C and includes several sections:

Health Information—General information about the status of the student's health, such as vomiting, fevers, or seizures.

Figure 11A:
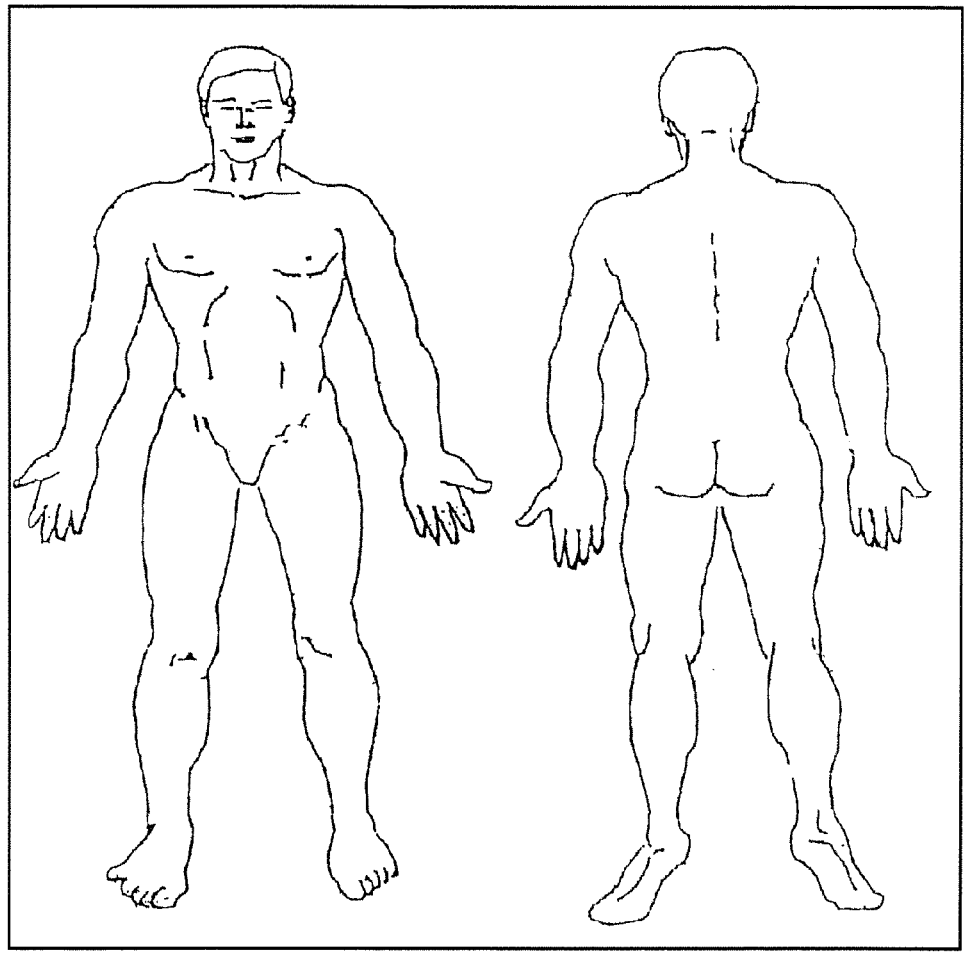
FIG. 11A is another exemplary screen display that may be presented by one or more computer programs of the present invention.
Figure 12:
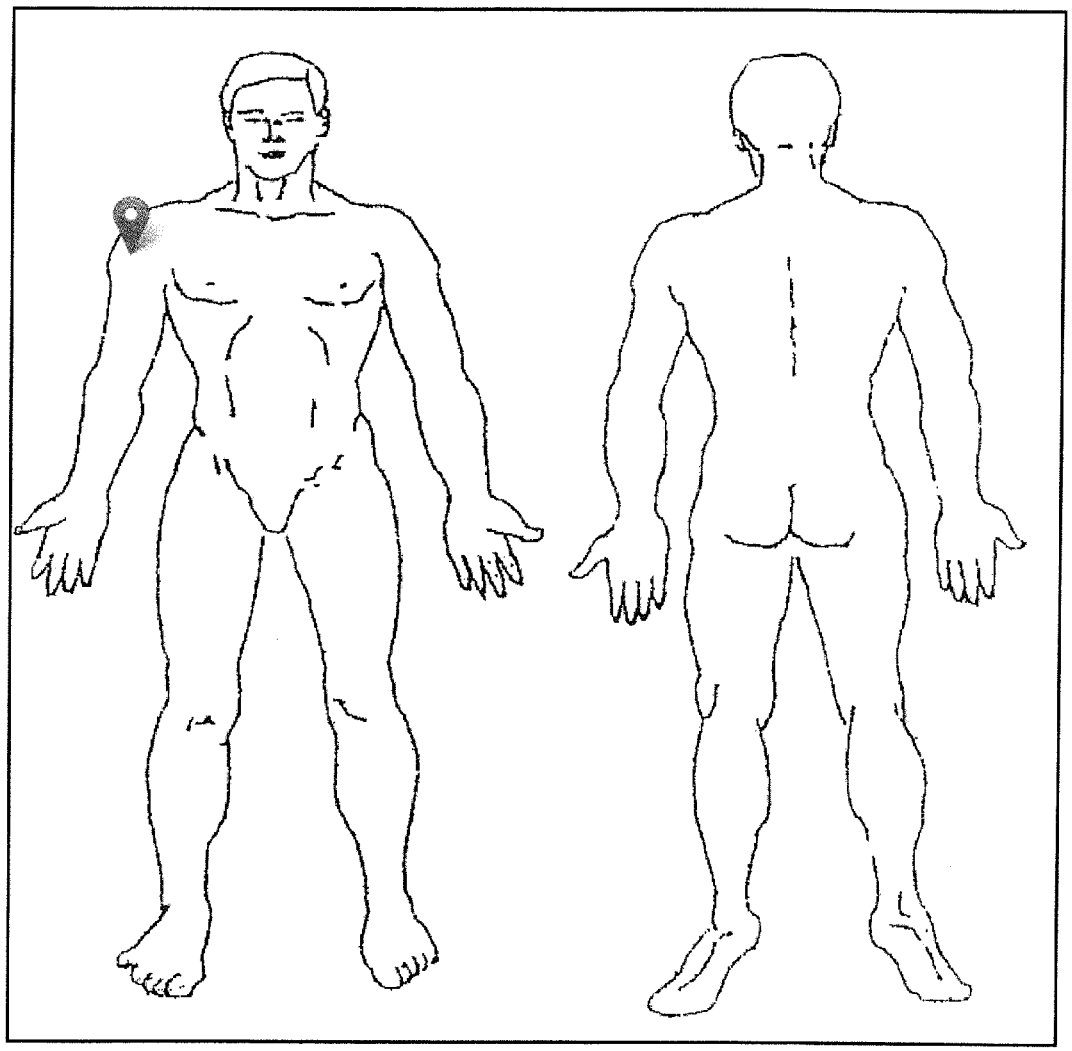
FIG. 12 is another exemplary screen display that may be presented by one or more computer programs of the present invention.

Weekly Skin Check—A moveable "map" of a person as depicted in FIG. 11A, and FIG. 12 that allows staff to place markers indicating any bruises, marks, or other abnormalities that the student is currently experiencing. The server tracks which staff member noted the problem and at what time. The "map" resets every week.

Meal Information—Information on the student's eating habits throughout the day, including what their menu is for that day. Staff can indicate if the student ate each meal (breakfast, lunch, and dinner), and also enter notes to indicate any special occurrences. In addition, the student can be designated as requiring "food records", which causes the system to insert a box next to each line of the student's menu. This allows staff to individually record for each item how much was eaten by the student (e.g. "two bites", "half").

Activity Log—This is a log of the activities that the student participated in throughout the day, both on and off campus. It includes options for activities such as "Movies", "Gym", and "Car Ride". There is also a notes field for staff to indicate other activities that are not typically included.

Sleep Information—This is a log of each hour from 9:30 PM-7:30 AM, allowing overnight staff to indicate if the student slept, woke up, required toileting, had a seizure, soiled their bed, and if a bed check was performed during that period. Some of this information is processed automatically to generate reports. For example, professional staff receive a report indicating if a student was up more than 2 consecutive periods during the night.

Morning, Classroom, and Evening Shift Information—These are sections with specific sections for each of the 3 shifts throughout the day. For example, the morning shift information section contains questions about the student's morning, if their bed has been made, what they brought to school, etc.

Clients

Figure 13:
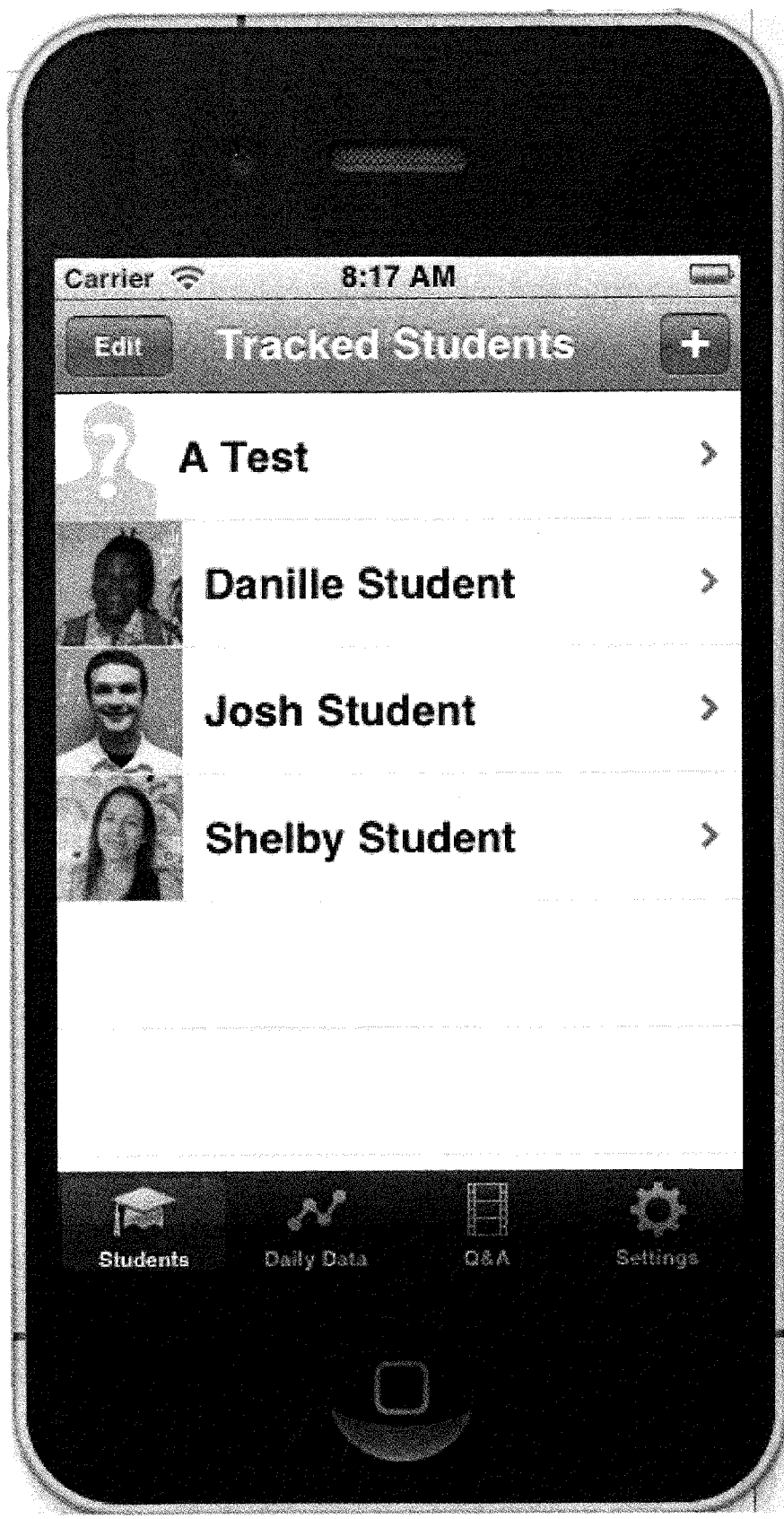
FIG. 13 is another exemplary screen display that may be presented by one or more computer programs of the present invention.

The clients or mobile clients are the portable electronic devices 12, 14 and the program or programs that run on them. The primary purpose of the client software is to provide information to the paraprofessionals and professional staff, and to collect data in real-time and send it to the server for analysis and reporting. An exemplary home screen of the client program is shown in FIG. 13. The client is comprised of several parts, each of which is represented by a tab along the bottom of the home screen.

The Students tab lists all the students that are currently being "tracked" by a mobile client as shown in FIG. 13. Users can add one or more students to be tracked by clicking an "Add" button and then choosing a student from a list o presented student names. A user may also choose a group of students to add from a presented list, wherein the students may be grouped by classroom, name, or other criteria. Adding a student causes the client to download the relevant information about the student from the server, including demographic information and information on what is to be tracked, including behavior trackers, therapy goals, medications, and communication log information. This information is based on the trackers set up by professional staff on the server. As professional staff update information on the server (for example, adding a new behavior to be tracked), the client automatically downloads the information in the background for any students which are being tracked by the client. By tapping on a student's name, the user can access detailed information about the student, including:

Profile information, such as parent and district contact information, team information, and other demographic information.

The student's daily schedule (as entered on the server by a paraprofessional.

A summary of the behaviors that have occurred for the day for that student.

The communication log for that student, which presents the same information as the server-side communication log, and allows mobile users to add and update information about the student's day.

Figure 14:
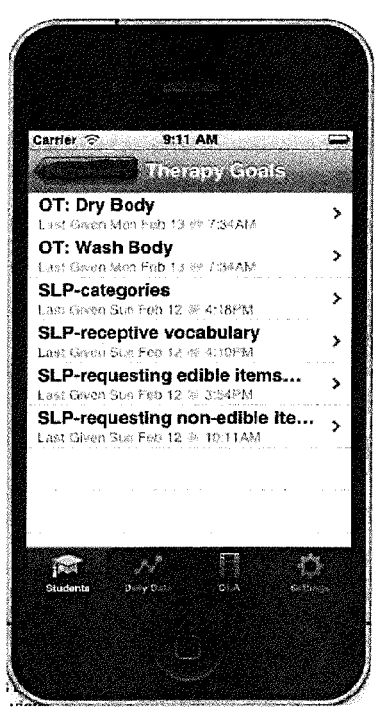
FIG. 14 is another exemplary screen display that may be presented by one or more computer programs of the present invention.
Figure 15:
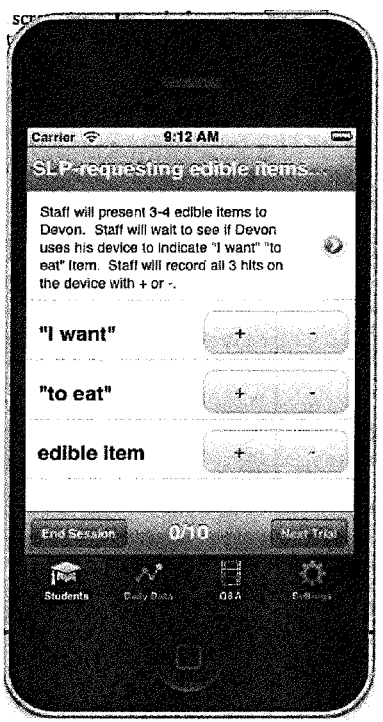
FIG. 15 is another exemplary screen display that may be presented by one or more computer programs of the present invention.
Figure 16:
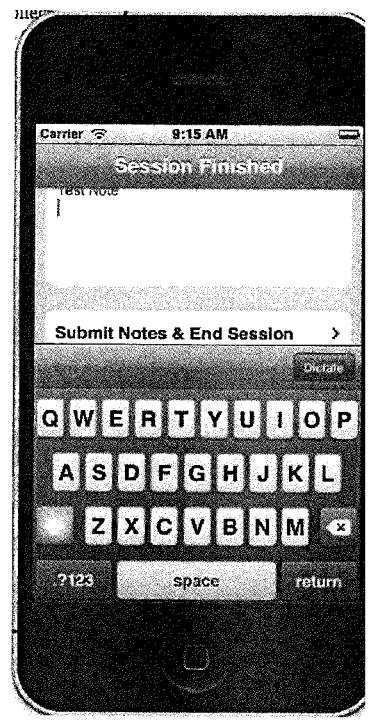
FIG. 16 is another exemplary screen display that may be presented by one or more computer programs of the present invention.

Under the Students tab, a user can also collect data while running therapy goals for the student. A list of available therapy goals is presented along with the time each goal was last run with the student as shown in FIG. 14. The user chooses a goal and is then presented with the data collection screen. The therapy data collection screen is comprised of a series of components that match the components set up by the professional staff on the server as shown in FIG. 15. The user designates a response for each of the components in each of several trials. After the correct number of trials has been performed, the user ends the session and can record notes which are viewable by the professional staff when analyzing the data as shown in FIG. 16. The data is then sent to the server for automatic analysis and reporting.

Figure 17:
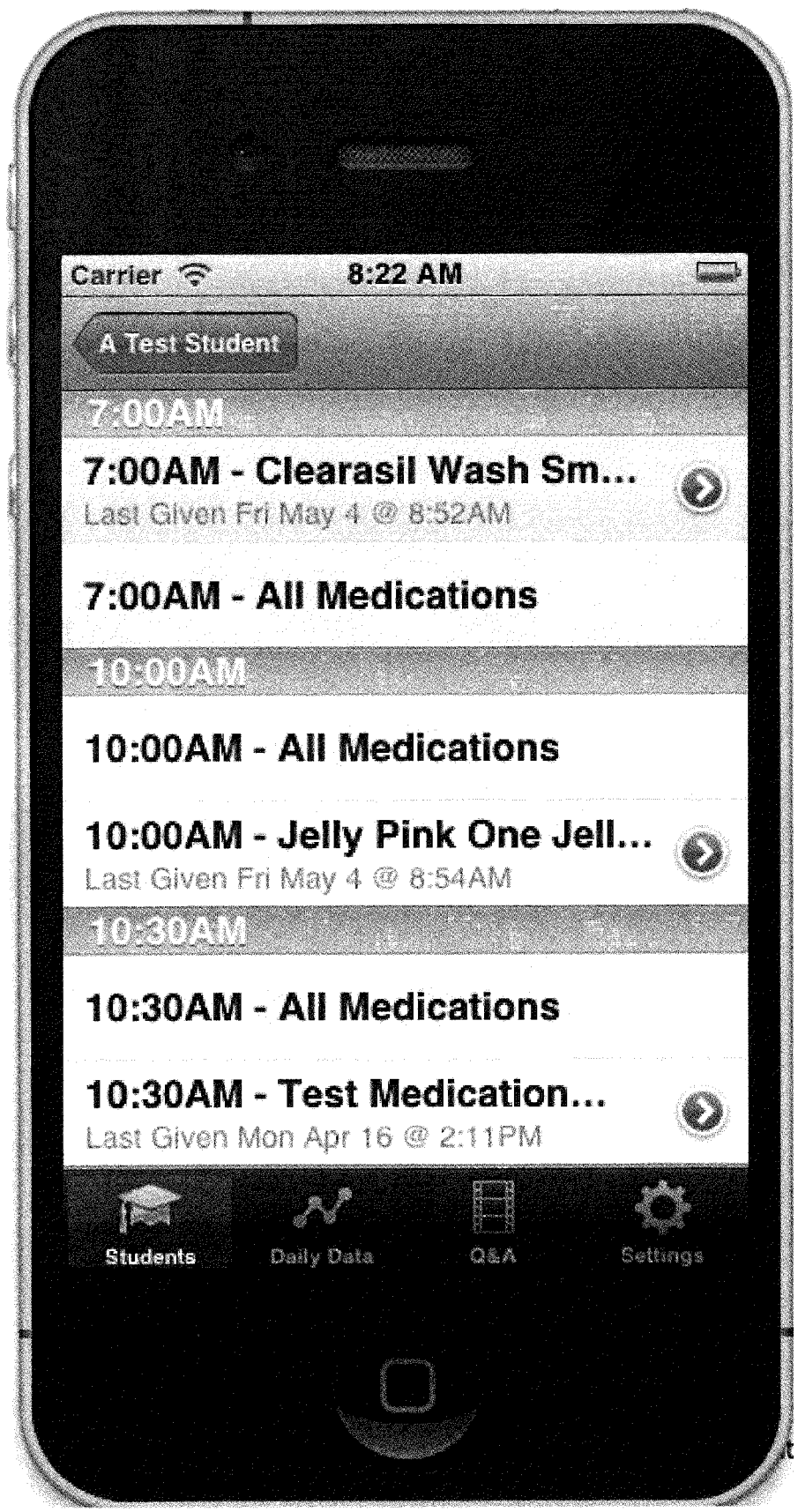
FIG. 17 is another exemplary screen display that may be presented by one or more computer programs of the present invention.

Paraprofessional or professional staff can also use the mobile clients to record when medications are administered to students. After tapping the Medications tab, the user is presented with a list of medications that have been entered by professional staff on the server as depicted in FIG. 17. Along with each medication, the time that it was last given (by any user, not just the current one) is displayed. The user may select the name of the medication they are going to administer. At this point, the client application checks to make sure that the medication is being given at the correct time, and if not, it alerts the user to make sure that they want to continue. In addition, if the medication is marked as "barcode required", the user must scan a QR code attached to the medication to continue. This scanning process also verifies that the correct medication is being given to the correct student. Finally, the user can enter any notes, as well as the initials of a "buddy" who is to check that the medication is administered properly. After submitting the report, the data is sent to the server for automatic analysis and later review by the professional staff. If professional staff is logged in to a portable electronic device and administering medication to a student, there are special provisions which allow them to override the need to scan a barcode, and they are also presented with an option to give all the medications for a specified time period with one tap instead of needing to tap each individual medication to give it.

Figure 18:
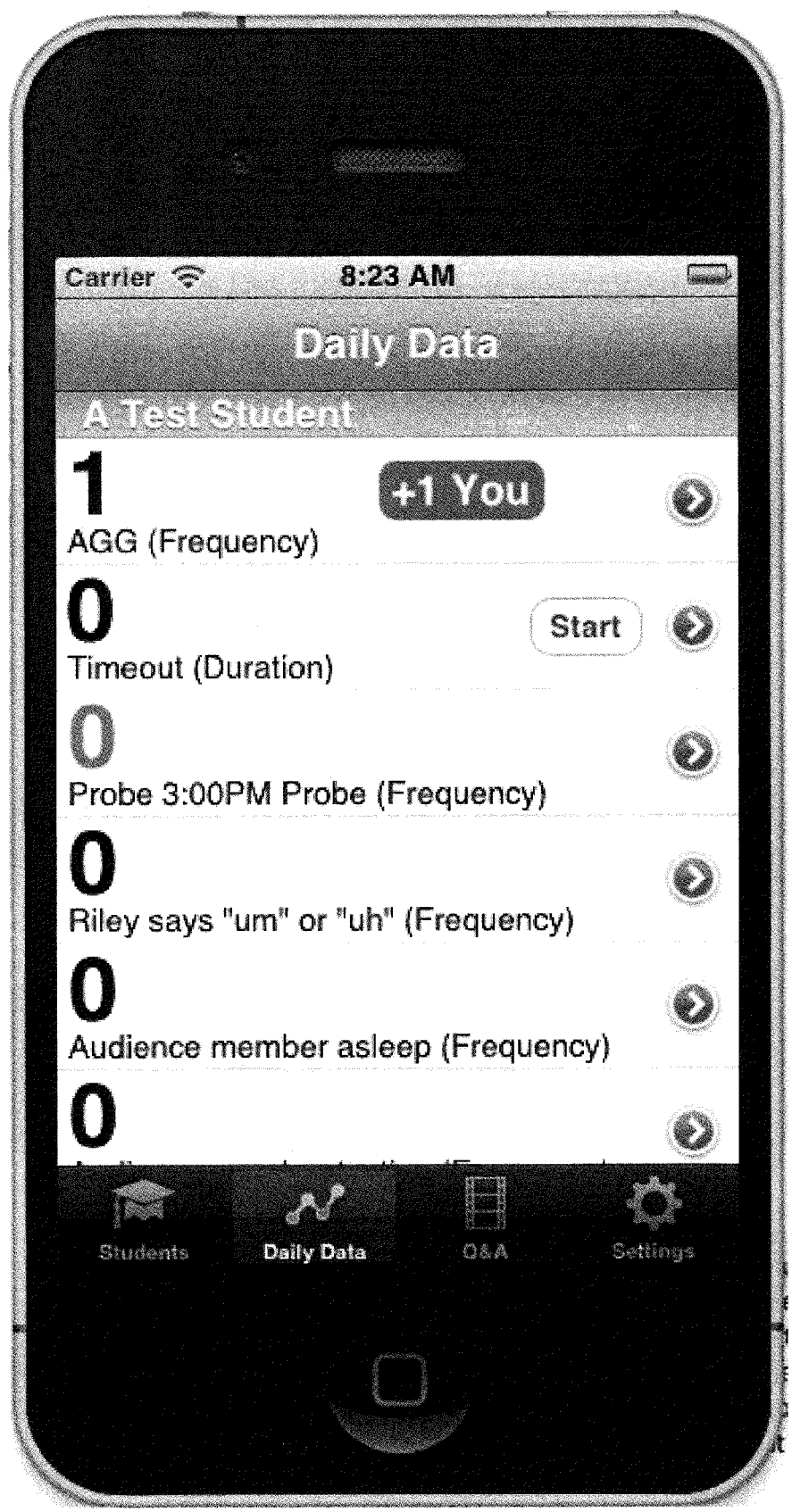
FIG. 18 is another exemplary screen display that may be presented by one or more computer programs of the present invention.

The Daily Data tab displays a screen shown in FIG. 18 that lists all of the current behaviors that are being tracked for a student as the professional staff has set them up on the server. For frequency count trackers, the user simply taps the name of the behavior each time it occurs. For duration trackers, the user taps the behavior once to start a timer that counts how long the behavior has been happening, and then taps again to stop the timer and record the data. After the data is recorded, it is sent to the server 16 for automatic analysis and later review by the professional staff.

Multiple paraprofessionals may be recording data on student behaviors at once, so the invention also features a real-time component to help reduce the amount of duplicate data reported. As data is taken, an alert is displayed via a blue bubble that appears in the behavior listing showing that data was just recorded by a paraprofessional for that behavior. This alert displays immediately on all portable electronic devices that are tracking the student, regardless of where the other staff member is located. The user can also tap a blue arrow next to the behavior name to access a list of previously recorded data for that behavior, which they can delete if the data was recorded incorrectly (e.g. an accidental tap). In addition, they can add "bulk" data (e.g. adding 50 to a frequency tracker) to accommodate students which may have behaviors more frequently than the user is able to enter them in real-time.

Figure 19:
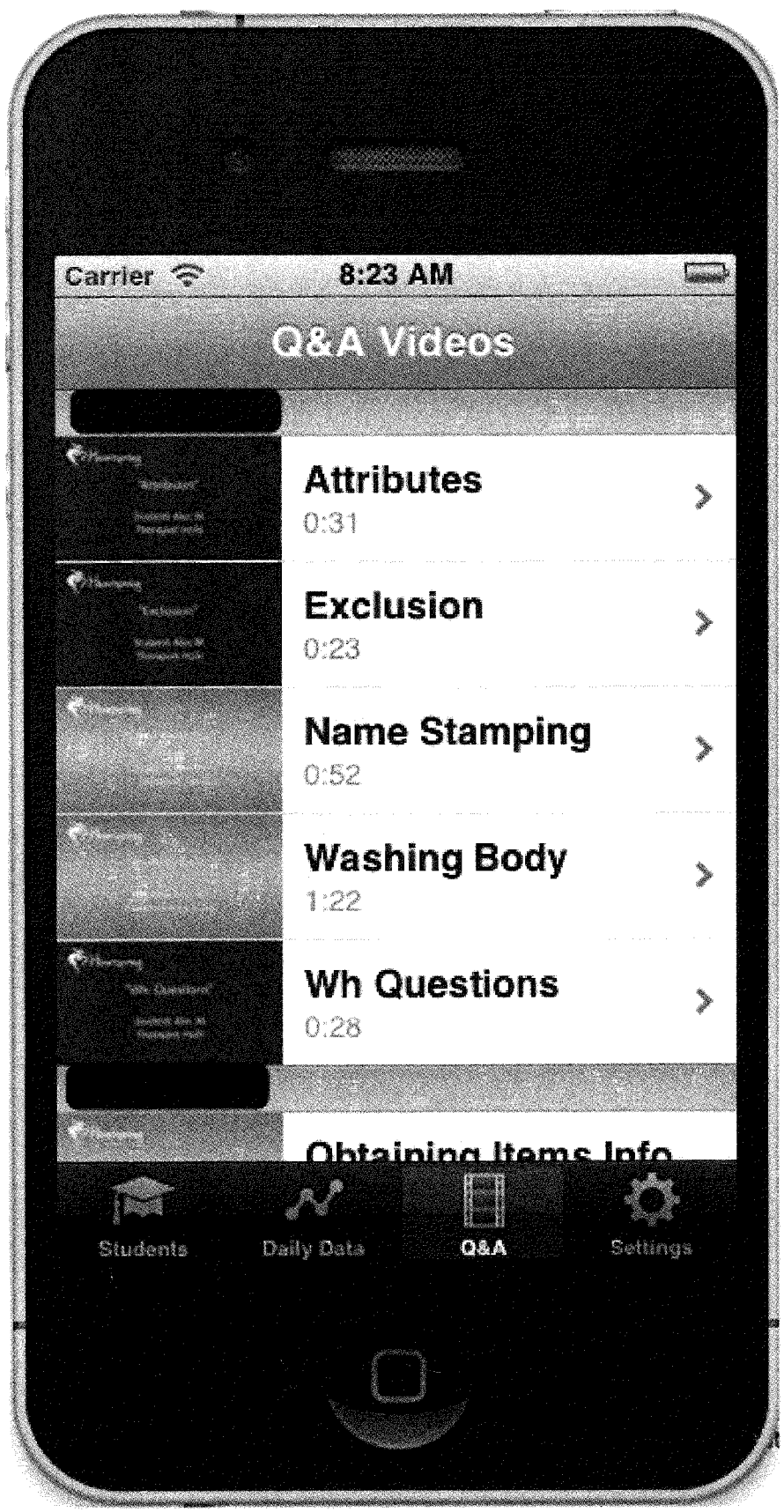
FIG. 19 is another exemplary screen display that may be presented by one or more computer programs of the present invention.

Many of the goals and behaviors that the students exhibit require specialized training to run and recognize. Paraprofessionals are frequently trained by professional staff, but trainings can only occur so often and there is a need for a quick "refresher" in-between trainings. Previously, paper directions and diagrams filled this need, but these could become quickly outdated, or might not communicate effectively. The invention provides a mechanism called "Q&A Videos" which allow professional staff to record short refresher courses on commonly asked questions regarding therapy goals, behaviors to be tracked, etc. These videos are then made available to paraprofessionals via the mobile application. The user can see a list of available videos, grouped by student, for the students they are currently tracking by tapping the Q&A tab as shown in FIG. 19. They can choose to watch the videos on-demand at any time. The number of times that a user watches a video is recorded so that professional staff can determine if a video is effective when they train paraprofessionals.

Many times, data must be collected by paraprofessionals while they are with students off campus, in an area without an Internet connection available. The mobile clients are designed to be fault-tolerant regarding connections to the server. Data collected regarding behaviors, medications, and therapy data is cached locally on the portable electronic devices 12, 14 until a connection can be established with the server. Once a connection is established, all of the cached data is sent to the server. The portable electronic devices can in theory remain without a connection to the server indefinitely, and in practice often goes 8+ hours between server syncs. This allows the data collection to happen anywhere the student is, rather than being restricted to only on-campus locations.

As mentioned above, embodiments of the invention are designed to facilitate collection of data by multiple persons simultaneously by:

- Allowing an unlimited number of mobile clients to track students at the same time.
- Syncing data to the server and then updating the mobile clients whenever data has changed.
- Informing other users when data is collected on a student they are tracking, via real-time alerts.
- Informing users when the last time a medication was given or a therapy goal was run with a student by any staff member.
- Providing tools for professional staff to correct and/or delete data after it is collected. The system tracks what modifications are made to the data, when they are made, and who made them, to serve as an audit trail.

The present invention also provides mechanisms to reduce duplicate or redundant data:

- As data is sent to the server in real-time, a notification of the collected data is sent to all connected mobile clients, resulting in the display of a "bubble" notification. For example, if John and Mary are collecting data on student Billy, when John sends data that indicates an aggression has occurred, a bubble appears on Mary's mobile device to indicate that John collected data on the aggression. This helps prevent duplication of data caused by two staff members submitting data at once.
- During analysis of incoming data by the server, an algorithm determines the likelihood of a piece of data being duplicated (based on factors such as multiple staff members recording the same behavior within a certain time frame). If a piece of data is determined to be duplicate, it is discarded.

When reviewing data for a student, professional staff are able to see that data in aggregate, but can also choose to look at the individual pieces of data collected, which tells them which staff member collected the data, at what time, and where. Staff members can make modifications to these specific data points to correct for inaccuracies in the data.

The present invention also provides improved mechanisms for analyzing data after it has been collected. The server processes data as it arrives in real-time, and then acts on the data through a series of algorithms. Some examples of this real-time analysis include:

- Alerting professional staff when a behavior crosses a threshold of N occurrences in a specified time frame, or a behavior has lasted longer than N minutes.
- Alerting professional staff when a student has not been given medication at the correct time.
- Notifying professional staff if data seems "abnormal", based on factors including a rolling 10-day average for the data and the standard deviation for the data during the previous 10 days.

In some embodiments, the student data collected is accompanied by data representative of the staff member who collected the data, the time at which the data was collected, and the location where the data was collected. This data may be used to generate reports such as a heat map over a campus or other defined area showing where student behaviors are most prevalent. In addition, automatic alerts are triggered based on certain conditions, such as a student exiting out of a door during a time when they should be in a classroom, or a student getting too far away from a designated staff member.

The present invention is also unique in that it permits collection of data at any time and at any place. Rather than collecting behavior data as a "secondary" piece of information only when therapy is being performed with a student, the present invention provides for 24/7 collection of student data as a primary piece of information. Data collected during the same time frame (such as behavior data collected while a therapy session was in progress) can still later be linked together for joint analysis.

The present invention is also unique in that it enables the collection of data from a variety of disciplines, including psychology (behavior) data, therapy data, and medical data. The data from these different disciplines is shared during reporting and analysis to give a more complete picture of a student's progress. For example, when looking at a graph of behaviors, psychologists can choose to see annotations on the graph indicating when medications were changed, or if a student's communication device was broken. The server can also automatically calculate correlations for behaviors compared to inputs from other disciplines such as amount of sleep, meals eaten, etc.

Embodiments of the invention also provide an important way to check the validity of data being collected. Professional staff using a mobile client are able to turn on a "Blind Data" mode. They can then collect data as normal. Later when the data is analyzed, the server automatically matches up data collected by paraprofessionals to the data collected by professional staff in "Blind Mode". The server calculates the percentage accuracy of the paraprofessional, allowing the professional staff to assess the validity of the data being collected. Such "Inter-rater" reliability data can be collected both for behavior data and therapy data.

Some types of data can be collected by the server entirely autonomously. For example, a sensor can be placed under the mattress of students to determine if they are in-bed or out-of-bed. Another sensor can determine if the student has wet the bed. A location tracking system allows for automatic detection of elopements. These sensors connect to the server wirelessly to report data in real-time. This data is processed by the server in real-time along with data collected by staff Collecting data autonomously can reduce the total number of staff needed to work with the students and lessens the collection burden on staff that are present. In addition, data is guaranteed to be accurate and reported at the correct time. Other sensors may be provided, including:

Sensors to determine self-injurious behaviors of a student.
Sensors to determine the need for one-to-one staffing.
Sensors to monitor the student's health and wellness.
Sensors to determine when a student has dropped to the floor, and additional staff assistance may be necessary.
Sensors to monitor physiological signs as a precursor to maladaptive behaviors.

Although the invention has been described with reference to the preferred embodiment illustrated in the attached drawing figures, it is noted that equivalents may be employed and substitutions made herein without departing from the scope of the invention as recited in the claims. For example, although embodiments of the invention may be implemented with the computer and communications equipment described herein, the invention is not limited to this particular computer and communications equipment.

Having thus described the preferred embodiment of the invention, what is claimed as new and desired to be protected by Letters Patent includes the following:

The invention claimed is:

1. A non-transitory computer-readable medium storing a computer program for directing operating of a computer system for use in collecting data for special needs students, the computer program comprising:

a code segment for receiving data representative of an incident for a special needs student from a portable electronic device operated by a first person;
a code segment for sending a notification of the incident to a portable electronic device operated by a second person to prevent duplicate reporting of the incident by the first and second persons;
a code segment for receiving data representative of an incident from the second portable electronic device;
a code segment for merging the data from the first and second persons in a computer file for the student; and
a code segment for analyzing the merged data in an attempt to identify duplicate data for the same incident.

2. The non-transitory computer readable medium set forth in claim 1, wherein the incident is an action taken by the student selected from the group consisting of an act of aggression, an utterance, and a physical movement.

3. The non-transitory computer readable medium set forth in claim 1, wherein the notification comprises a description of the incident and an identification of the person who reported the incident.

4. The non-transitory computer readable medium as set forth in claim 1, further comprising a code segment for receiving from the portable electronic devices data representative of a date, time and location of the incidents.

5. The non-transitory computer readable medium set forth in claim 4, wherein the code segment for analyzing the merged data compares the date, time, and location of the incidents in an attempt to identify duplicate data.

6. The non-transitory computer readable medium set forth in claim 1, further comprising a code segment for analyzing the merged data and sending an alert to a portable electronic device operated by a professional staff when the data suggests a problem.

7. The non-transitory computer readable medium set forth in claim 6, wherein the alert is sent to the portable electronic device operated by the professional staff when a frequency of the incidents exceeds a threshold amount.

8. The non-transitory computer readable medium set forth in claim 6, further comprising a code segment for receiving data representative of the incident from the portable electronic device operated by the professional staff and comparing the data from the professional staff to the data from the first person to assess accuracy of the data from the first person.

9. A non-transitory computer-readable medium storing a computer program for directing operation of a computer system for use in collecting data for special needs students, the computer program comprising:

a code segment for receiving data representative of an incident for a special needs student from a portable electronic device operated by a first person;
a code segment for receiving data representative of an incident for the student from a portable electronic device operated by a second person;
a code segment for merging the data from the first and second persons;
a code segment for analyzing the merged data in an attempt to identify duplicate data for the same incident; and
a code segment for deleting any duplicate data that is identified.

10. The non-transitory computer readable medium set forth in claim 9, wherein the incident is an action taken by the student selected from the group consisting of an act of aggression, an utterance, and a physical movement.

11. The non-transitory computer readable medium set forth in claim 10, wherein the notification comprises a description of the incident and an identification of the person who reported the incident.

12. The non-transitory computer readable medium set forth in claim 9, further comprising a code segment for sending a notification of the incident reported by the first person to the portable electronic device operated by the second person to prevent duplicate reporting of the incident by the first and second persons.

13. The non-transitory computer readable medium set forth in claim 9, further comprising a code segment for receiving from the portable electronic devices data representative of a date, time and location of the incidents.

14. The non-transitory computer readable medium set forth in claim 13, wherein the code segment for analyzing the merged data compares the date, time, and location of the incidents to identify the duplicate data.

15. A system for collecting and analyzing data for special needs students, the system comprising:
- a server programmed to receive profile information for each of the students including behaviors to monitor for each of the students;
- a plurality of portable electronic devices operated by persons caring for the children, wherein each portable electronic device is programmed to receive some of the profile information for a student from the server, display some of the behaviors to be monitored for the student; receive data representative of a monitored behavior, and transmit the data to the server for analysis by the server; and
- wherein the server is programmed to simultaneously receive data representative of monitored behaviors from multiple of the portable electronic devices and to identify and delete duplicate data.

16. The system as set forth in claim 15, wherein the server is programmed to identify duplicate data by comparing when, where, and by whom the monitored behaviors were observed.

* * * * *